United States Patent [19]
Becker

[11] 3,980,679
[45] Sept. 14, 1976

[54] PROCESS FOR THE MANUFACTURE OF GLYCIDYL ETHERS OF MONOHYDRIC OR POLYHYDRIC PHENOLS, HAVING IMPROVED PROPERTIES

[75] Inventor: Wilhelm Becker, Hamburg, Germany

[73] Assignee: Hoechst Aktiengesellschaft, Germany

[22] Filed: Jan. 17, 1974

[21] Appl. No.: 433,995

[30] Foreign Application Priority Data
Jan. 29, 1973  Switzerland............. 1219/73
Oct. 9, 1973  Switzerland............ 14340/73

[52] U.S. Cl. .................................... 260/348.6
[51] Int. Cl.² ............................. C07D 301/28
[58] Field of Search ......................... 260/348.6

[56] References Cited
UNITED STATES PATENTS
2,995,583  8/1961  Larkin et al. ............. 260/348.6
3,766,221  10/1973  Becker ..................... 260/348.6

FOREIGN PATENTS OR APPLICATIONS
2,108,207  10/1971  Germany
1,961,888  7/1970  Germany
6,908,790  12/1970  Netherlands............... 260/348.6

OTHER PUBLICATIONS
Chemical Abstracts, vol. 76 (1972) 60444b.

*Primary Examiner*—Norma S. Milestone
*Attorney, Agent, or Firm*—Gordon W. Hueschen

[57] ABSTRACT

The invention relates to a process for the manufacture of glycidyl ethers of monohydric or polyhydric phenols with excess epichlorohydrin, wherein the monohydric or polyhydric phenols are reacted with excess epichlorohydrin, based on the phenolic hydroxyl group, in the presence of a catalyst specific for the formation of chlorohydrin ethers from phenols and epichlorohydrin, and of 0.2 to 8 % by weight of water, based on the reaction medium, until the conversion to chlorohydrin ethers is at least 10 %, preferably 50 – 90 %, based on the phenolic hydroxyl groups, and are then reacted by heating with 0.9 to 1.15 equivalents of a solid alkali metal hydroxide per phenolic hydroxyl group to give glycidyl ethers.

8 Claims, No Drawings

PROCESS FOR THE MANUFACTURE OF GLYCIDYL ETHERS OF MONOHYDRIC OR POLYHYDRIC PHENOLS, HAVING IMPROVED PROPERTIES

BACKGROUND OF THE INVENTION

1. Field of the invention

The invention relates to a process for the manufacture of low molecular monoglycidyl ethers or polyglycidyl ethers of monohydric or polyhydric phenols, having improved properties.

By improved properties there is understood that these glycidyl ethers, obtained by the process:

1. display a low intrinsic colour of the glycidyl ethers, expressed by low values of the Hazen colour index [ASTM D 1209 / 62, Pt/Co- Standard: Hazen Standard (APHA)] and 2. a low content of hydrolysable chlorine.

2. Prior art

Processes are known which provide an after-treatment of glycidyl compounds for lightening the colour but which imply an additional process step and are rather ineffective in the case of products which are already relatively strongly coloured.

German Auslegeschrift 1,238,918 describes a process of stabilisation of epoxide compounds against discolourations, for example through heat exposure, by addition of 0.05 to 3.0% of organic peroxides. However, this process applies to measures during subsequent use of the epoxide compounds.

Swiss Patent Specification No. 442,262 describes a process for the manufacture of solid polyglycidyl ethers which on average possess more than one epoxy group per molecule and have a Durrans softening point of at least 50°C, the process being carried out in the presence of sodium dithionite and/or under a nitrogen atmosphere. This procedure, which inherently is only intended for use in the manufacture of higher-molecular polylycidyl ethers, however only gives products of Hazen colour indices of 100–150 and such values are even attainable without the recommended measures if the starting substances are of perfect quality.

The patent literature describes several processes for the manufacture of glycidyl ethers which use catalysts for the chlorohydrin ether formation. The processes are in some cases very involved and the products of the process also do not have the desired low chlorine contents.

According to the process described in USA Patent Specification No. 3,336,342, polyhydric phenols are reacted with epihalogenohydrins in the presence of sulphonium salts, or compounds containing sulphur which can react with epihalogenohydrin to give sulphonium salts, to form the corresponding halogenohydrins from which, after removing the excess epihalogenohydrin, hydrogen halide is split off so as to arrive at the desired epoxide compounds. This process is very time-consuming, since the formation of the chlorohydrin ether requires at least 40 hours. Furthermore, the excess epihalogenohydrin distilled off contains some dihalogenohydrin and must be worked up separately before being reused. For these reasons the process is very time-consuming, involved and uneconomical.

According to the process described in USA Patent Specification No. 3,372,142, not only carboxylic acids but also phenols are converted into the chlorohydrin compounds by means of excess epichlorohydrin in the presence of benzyltrimethylammonium chloride or anionic exchanger resins and thereafter converted into the epoxide comounds with an aqueous solution of an alkali metal hydroxide which is saturated with an alkali metal carbonate. Here again it is found that the process is muct too time-consuming for practical use since the formation of the chlorohydrin ether required 25 hours. Including the working up of the chlorohydrin ether to give the epoxide compound, which would require a further 10–15 hours, the kettle dwell time would be unacceptable in practice.

A similar process is described in USA Patent Specification No. 2,943,096, accordingn to which, again, polyhydric phenols and epichlorohydrin are converted into the chlorohydrin ether, in the presence of tetramethylammonium chloride or benzyltrimethylammonium chloride. This again requires 25 hours. The further working up of the reaction batch proves to be very expensive since the excess epichlorohydrin, after being separated off by distillation, must be worked up with sodium hydroxide solution because of its dichlorohydrin content, to give a purer epichlorohydrin which can be reused. The chlorohydrin ether isolated is dissolved in a solvent mixture of toluene/ethanol and converted into the glycidyl ether by reaction with 18% strength by weight aqueous sodium hydroxide solution. Here again the individual process steps require a great deal of time so that this process cannot be regarded as very economical.

According to the data in Netherlands Published Specification 69/08790 excess epichlorohydrin is reacted, in a first stage, with a polyphenol in the presence of a catalyst, for example a quaternary ammonium salt to give the chlorohydrin ether, the conversion being at least 80% and preferably at least 90%, relative to the phenolic OH groups. In the second stage, an aqueous sodium hydroxide solution which contains 0.80 to 0.99 equivalent of sodium hydroxide per phenolic OH group is added, water being distilled off azeotropically. The glycidyl ether is additionally subjected to a post-dehalogenation.

According to the disclosures in Netherlands Published Specification 70/08287 excess epichlorohydrin is reacted, in a first stage, with a polyphenol in the presence of a catalyst, for example a quaternary ammonium salt, to the chlorohydrin ether, the conversion being at least 5%, but less than 80%, relative to the phenolic OH groups. In the second stage, an aqueous sodium hydroxide solution which contains 0.80 to 0.99 , preferably 0.92 to 0.98, equivalent of sodium hydroxide per phenolic OH group is added, water being distilled off azeotropically whilst recycling the dehydrated epichlorohydrin. The glycidyl ether is additionally subjected to a post-dehalogenation. The quoted contents of easily saponifiable chlorine in the resulting products of the process are between 0.75 and 0.20% by weight.

It is the task of the present invention to provide a process for the manufacture of glycidyl ethers of monohydric or polyhydric phenols having low contents of hydrolysable chlorine, which gives excellent results even on an industrial scale and can be carried out in an economically advantageous manner.

SUMMARY

The subject of the invention is a process for the manufacture of glycidyl ethers of monohydric or polyhydric phenols with excess epichlorohydrin, wherein the monohydric and polyhydric phenols are reacted with excess epichlorohydrin, based on the phenolic hydroxyl group, in the presence of a catalyst specific for the formation of chlorohydrin ethers from phenols and epichlorohydrin, and of 0.2 to 8% by weight of water, based on the reaction medium, until the conversion to chlorohydrin ethers is at least 10%, preferably 50–90%, based on the phenolic hydroxyl groups and are then reacted by heating with 0.9 to 1.15 equivalent of a solid alkali metal hydroxide per phenolic hydroxyl group, to give glycidyl ethers, characterised in that, in the presence of 0.001 to 5, preferably 0.01 to 1, % by weight, based on the amount of phenol employed, of a divalent tin compound a. in a first stage, at least 10%, and preferably 50 – 90%, based on the phenolic hydroxyl groups, of chlorophydrin ethers are formed in an alkali-free medium and thereafter b. 10 to 90% by weight, preferably 15 to 50% by weight, of the solid alkali metal hydroxide are added to the reaction mixture over the course of 8 to 90%, preferably 15 to 50%, of the total time of addition of the solid alkali metal hydroxide, which is 30 to 300, preferably 90 to 180, minutes, with removal of the heat of reaction by cooling or by distillation under reflux under reduced pressure in the presence of water of reaction and, if appropriate, added water, and thereafter c. 90 to 10% by weight, preferably 85 to 50% by weight, of the solid alkali metal hydroxide are added in 92 to 10%, preferably 85 to 50%, of the total time of addition of the solid alkali metal hydroxide, with removal of the heat of reaction, of the water of reaction and, if relevant, of the added water, by azeotropic distillation, and thereafter d. the excess epichlorohydrin is distilled from the glycidyl ether formed and, if the resulting glycidyl ether contains more than 0.1% by weight of saponifiable chlorine, the ether is dissolved in an inert solvent and subjected to a further dehydrochlorination with the aid of excess aqueous alkali metal hydroxide solution, relative to the hydrolysable chlorine present.

In a special embodiment of the invention the azeotropic distillation in step c) is carried out by recycling of the phase containing epichlorohydrin, which has been freed from water, to the reaction mix.

In a further special embodiment of the invention the water of reaction is distilled off (optionally the added water) and the non-reacted epichlorohydrin or the phase containing epichlorohydrin, which has been freed from water, is not returned to the reaction mixture in step (c).

As a result of the fact that in the special embodiment of stage (c) the water of reaction removed during the azeotropic distillation (the optionally added water) and the unreacted epichlorohydrin are not recycled to the reaction vessel, the production of the diglycidyl ether is substantially accelerated. The distillation time is on average reduced by about 25% by this modified procedure.

The achievable Hazen colour indices of the glycidyl ethers obtained according to the process are below 50 on this colour index scale. With glycidyl ethers of bisphenol A having such colour indices it is possible, provided epoxide resin curing agents of correspondingly light colour are used, to deal with applications which were previously reserved to unsaturated polyesters but for which the latter could only be used with reservations because of their less favourable chemical resistance and mechanical properties. Such end uses are, for example, potting of electrical, anatomical and other objects, white-pigmented coatings and paints.

The glycidyl ethers contain less than 0.1% by weight of easily saponifiable chlorine. The improved glycidyl ethers produced can therefore be employed with particular advantage for the manufacture of compression moulding compositions and for encasing and potting in the electrical field, where resins of higher chlorine content show poorer stability, particularly in the simultaneous presence of heat and moisture.

It is a further task of the invention to provide an improved process by which glycidyl ethers of monohydric or polyhydric phenols can be obtained in a very pure form by reaction of the phenolic OH groups with excess epichlorohydrin in the presence of catalysts and alkali, with shortest possible kettle dwell times.

It is furthermore possible, in this process, in every case to re-employ the distillate obtained after the condensation, after making up the consumed amount of epichlorohydrin and distillation losses, without rectifying the distillate and without an adverse effect on the condensation products. This for the first time ever permits rationalised manufacture of the glycidyl ether.

The new process is further distinguished in that the yield almost corresponds to the glycidyl ether which should be produced theoretically. Furthermore, secondary epichlorohydrin losses through undesired side-reactions, such as, for example, the polymerisation of the epichlorohydrin or formation of ether from epichlorohydrin in the presence of alkali, are depressed to a minimum by the lower reaction temperature of 50° to 100°C, preferably 75° to 95°C, which is employed.

Suitable divalent tin compounds are above all compounds which can form stannites ($Me^I_2[Sn(OH)_4]$ or $Me^I[Sn(OH)_3]$) with alkalis, such as $SnCl_2$, $Me^I[SnCl_3]$, $SnCl_2.2H_2O$, $SnF_2$, $SnBr_2$, $SnI_2$, $Sn(OH)_2$, $SnSO_4$, $Sn(NO_3)_2$, $Sn(SCN)_2$, $SnC_2O_4$(oxalate) and salts of divalent tin with organic acids, of the formula $Sn(OOCR)_2$, wherein -R can be an alkyl or iso-alkyl radical with 1 to 12 C atoms, or the stannites themselves. "Tin salt", $SnCl_2. 2H_2O$, is used preferentially.

The action of the divalent tin salt can be assisted by using a protective gas such as nitrogen, especially in the process steps in which a vapour phase does not form above the reaction mixture.

As monohydric or polyhydric phenols it is possible to use: Phenol, o-, m- and p-cresol, 1,2,4-, 1,2,6-, 1,2,3-, 1,2,5-, 1,3,4- and 1,3,5-xylenol, p-tertiary butylphenol, o-, m- and p-phenylphenol, the isomeric amylphenols, octylphenols and nonylphenols, pyrocatechol, resorcinol, hydroquinone, 1,4-dihydroxynaphthalene and other dihydroxynaphthalenes, 4,4'-dihydroxydiphenyl, 2,2'-dihydroxydiphenyl and other isomeric dihydroxydiphenyls, 2,2'-, 2,4'- and 4,4'-dihydroxydiphenylmethane individually or as mixtures (also referred to as bisphenol F), 4,4'-dihydroxydibenzyl, and substituted dihydroxydiphenylmethanes such as are produced by acid condensation of phenols with aldehydes or ketones, especially 4,4'-dihydroxy-diphenyl-2,2-propane, so-called diphenylpropane or bisphenol A, which can be prepared from phenol and acetone, and also dihydroxydiphenylcyclohexane. As further examples there may be mentioned: 4,4'-Dihydroxy-3,3',5,5'-tetramethyldiphenylmethane, 4,4'-dihydroxy-3,3',5,5'-tetramethyldiphenyl-2,2-propane, 4,4'-dihydroxy-3,3',5,5'-tetra-p-tert.-butyldiphenyl-methane, 4,4'-dihydroxy-3,3',5,5'-tetra-p-tert.-butyl-diphenyl-2,2-propane, 4,4'-dihydroxy-3,3'-dimethyl-5,5'-di-p- tert.-butyldiphenylmethane, 4,4'-dihydroxy-3,3'-dimethyl-5,5'-di-p-tert.-butyl-diphenyl-2,2-propane, 4,4'-dihydroxy-3,3',5,5'-tetraamyl-diphenylcyclohexane, 4,4'-dihydroxy-3,3',5,5'-tetra-p-tert.-butyldiphenyl-cyclohexane and 4,4'-dihydroxy-3,3'-dimethyl-5,5'-di-p-tert.-butyl-diphenyl-cyclohexane.

The polyhydric phenols used as starting substances can also contain other substituents or functional groups in the molecule in addition to the phenolic hydroxyl groups, for example hydrocarbon radicals, ether groups, ester groups, halogen atoms, hydroxyl groups and others, provided this does not interfere with the reaction. Accordingly it is possible to use: 4,4'-Dihydroxydiphenylsulphone, tetrabromobisphenol, tetrachlorobisphenol, chlorohydroquinones, methylresorcinol and phloroglucinol.

It is also possible to use polyhydric phenols, for example novolak resins, which are obtained by acid-catalysed condensation of phenol, p-cresol or other substituted phenols with aldehydes, such as formaldehyde, acetaldehyde, crotonaldehyde, i-butyraldehyde, i-nonylaldehyde and the like, condensates of phenols with cardanol, such as are described in USA Patent Specification No. 2,317,607, condensates of phenols with aliphatic diols, such as are described in USA Patent Specification No. 2,321,620 and condensates of phenols with unsaturated fatty oils, such as are described in USA Patent Specification No. 2,031,586.

The above list of the compounds which are suitable for use as starting substances is not exhaustive. A detailed list of the possible compounds is contained, for example, in the book "Epoxydverbindungen und Epoxydharze" ("Epoxide Compounds and Epoxide Resins") by A.M. Paquin, Springer-Verlag, 1958, pages 256–307.

Phenol, p-tertiary butylphenol, bisphenol A, bisphenol F and tetrabromobisphenol are employed preferentially.

In another embodiment, a mixture of 0.60 to 0.99 mol of bisphenol A and 0.40 to 0.01 mol of a diphenol from the group of the abovementioned compounds, especially hydroquinone, resorcinol, bisphenol F and novolak resins which are obtained by acid-catalysed condensation of phenol and aldehydes, such as formaldehyde, acetaldehyde, crotonaldehyde and i-butyraldehyde, is used to manufacture the diglycidyl ethers of low viscosity (6,000 to 16,000 cP/25°C) to prevent crystallisation of these products on prolonged storage in cool areas.

The monohydric or polyhydric phenols employed should have as slight an intrinsic colour as possible: for example, the Hazen colour index of a 30% strength by weight solution of bisphenol A in methanol should be less than 50.

Alkali metal hydroxides in the sense of the invention are also to be understood as alkali metal hydroxides which contain up to 5% by weight of alkali metal carbonate, or mixtures of alkali metal hydroxide and alkali metal carbonate, wherein the alkali metal carbonate content should be at most 5% by weight.

Alkali metal hydroxides which can be used are the solid compounds in the form of granules, flakes or powders, sodium hydroxide being the preferred alkali metal hydroxide. The hydroxides can be added by means of known devices, such as metering screws or bucket-wheel locks, as have previously been described, for example in the book by Jan Pinkava "Laboratoriumstechnik kontinuierlicher chemischer Prozesse", ("Laboratory Technique for Continuous Chemical Processes"), Verlag Harri Deutsch, Frankfurt/Main 1962, pages 144–146.

3 to 15, preferably 4 to 12, mols of epichlorohydrin are employed in the reaction per phenolic OH group. As specific catalysts for the formation of chlorohydrin ethers from phenolic hydroxyl and epichlorohydrin it is possible to employ: Choline, choline chloride, choline citrate, choline hydrogen citrate, choline hydrogen tartrate or other choline salts, in a solid or dissolved form or mixed with inorganic or organic substrates, and further quaternary ammonium salts.

Choline or choline chloride are employed preferentially. The catalyst is employed in amounts of 0.05 to 5% by weight, perferably 0.1 to 1% by weight, relative to the phenolic component.

The reaction can be carried out in the presence of 3 to 25 percent by weight of an alcohol of limited solubility in water, such as n-butanol, i-butanol, secondary butyl alcohol and the various isomeric pentanols, or hexanols, preferably i-butanol or n-butanol, the preferred amounts of the alcohol being 5 to 10% by weight, relative to the amount of epichlorohydrin employed. This addition of the alcohols of limited solubility in water is advisable in order to improve the removal of water in stage c. For the same purpose, the reaction can also be carried out in the sole presence, or in the presence additional to the aliphatic alcohols of limited solubility in water, of 3 to 25 percent by weight of aromatic solvents, such as benzene, toluene, xylene and others, but preferably xylene.

In all cases it is important that 0.2 to 8 percent by weight of water should be present at the beginning and during the first two sections of the reaction. The elimination of HCl is carried out by reaction with 0.90 to 1.15 equivalents of a solid alkali metal hydroxide per equivalent of phenolic hydroxyl group, which is added in portions or continuously at 50° to 110°C, preferably 75° to 95°C, in 30 to 300 minutes, an azetropic dehydration being carried out in stage c.

After addition of the alkali metal hydroxide, preferably sodium hydroxide, a part of the excess epichlorohydrin and, if relevant, of the additional solvent - say 10 to 30% by weight of the amount employed - is distilled off under reduced pressure at a temperature of 60° to 70°C, the metal halide formed in the reaction is then filtered off and the mixture is further concentrated in vacuo whilst heating, up to 120°C. To remove slight amounts of impurities, the liquid glycidyl ether can be filtered once more, or excess epichlorohydrin and, if relevant, the additional solvents of limited solubility in water, are removed by means of a vacuum at temperatures which are initially 60°C and finally 120°C. The reaction product is then taken up in a suitable solvent, such as acetone, methyl isobutyl ketone, benzene, toluene or xylene, and the alkali metal chloride is eluted with water. The glycidyl ether solution is dehydrated by azeotropic distillation, if appropriate after neutralising the solution to a pH value of 6.0 to 8.0, and is concentrated in vacuo until the temperature reaches 150°C. The liquid glycidyl ether can then be additionally freed of impurities by filtration.

In a particular embodiment, the last remnants of organic solvents are removed from the liquid glycidyl ether by a steam distillation at temperatures of 100 to 180°C, preferably 140° to 160°C, if appropriate by means of a vacuum.

In another embodiment, the volatile constituents are removed from the liquid glycidyl ether which has been heated to 100°–180°C, preferably 140° to 160°C, by allowing 10 to 1% by weight, preferably 6 to 3% by weight, relative to the glycidyl ether, of aqueous hydrogen peroxide solution ($H_2O_2$ content: 1 to 20% by weight, perferably 3 to 6% by weight) to run into the mixture, whilst stirring.

The following examples 1 to 18 explain the process in more detail, in which in stage (c) a recycling of the phase containing epichlorohydrin, which has been freed from water, is carried out.

EXAMPLE 1

330 g of bisphenol A, 1,610 g of epichlorohydrin, 32 g of xylene, 48 g of water, 0.33 g of $SnCl_2.2H_2O$ and 1.5 ml of choline chloride, as a 70% strength solution in water, were warmed for 2 hours to 95°C in a three-neck flask. 124 g of sodium hydroxide (containing at least 98% by weight of NaOH) were then added uniformly distributed over 2 hours, at the same temperature, the reaction mixture first being kept under a reflux condenser. 30 minutes after starting the addition of sodium hydroxide the water was removed azeotropically, again at 95°C, under a slight vacuum, the epichlorohydrin phase freed of the water being recycled to the reaction mixture. After completion of the addition of sodium hydroxide, the epichlorohydrin and solvent were removed under a waterpump vacuum of approx. 15 mm Hg. The residue was then kept under this vacuum for approx. 1 hour at 120°C. Thereafter the residue was dissolved in 500 g of xylene. The sodium chloride formed was washed out with 660 g of water. If the content of saponifiable chlorine in the glycidyl ether obtained exceeded 0.1% by weight, the product was subjected to a further dehydrochlorination with 115 g of a 10% strength by weight aqueous sodium hydroxide solution for 1 hour at 95°C.

The aqueous phase was removed and the xylene solution was neutralised with dilute phosphoric acid, freed of the water by azeotropic circulatory distillation, filtered and concentrated under a vacuum of approx. 15 mm Hg whilst raising the temperature to 120°C. The bisphenol A-glycidyl ether was left under this vacuum at 120°C for 60 minutes. A bisphenol A-glycidyl ether having an epoxide equivalent of 175, a viscosity of 7,180 cP measured at 25°C, an 0.04% by weight content of easily saponifiable chlorine and a Hazen colour index of 30 was obtained.

EXAMPLE 2

Example 1 was repeated with the modifications that
1. 10 minutes after beginning the addition of sodium hydroxide, the azeotropic removal of water and recycling of the epichlorohydrin phase, which had been freed of the water, to the reaction mixture was commenced and
2. it was possible to dispense with the further dehydrochlorination.

A bisphenol A-glycidyl ether having an epoxide equivalent of 176, a viscosity of 6,930 cP measured at 25°C, an 0.08% by weight content of easily saponifiable chlorine and a Hazen colour index of 30 was obtained.

EXAMPLE 3

Example 1 was repeated with the modifications that
1. the reaction mixture did not contain any xylene and
2. before starting to add the sodium hydroxide the mixture was kept for 3 hours at 95°C. In carrying out this example, further dehydrochlorination was used. A bisphenol A-glycidyl ether having an epoxide equivalent of 174, a viscosity of 8,100 cP measured at 25°C, a content of easily saponifiable chlorine of less than 0.1% by weight and a Hazen colour index of 35 was obtained.

EXAMPLE 4

Example 1 was repeated, with the modifications that
1. instead of 32 g of xylene, 32 g of i-butanol were present in the reaction mixture and
2. 60 minutes after starting the addition of sodium hydroxide, the azeotropic removal of the water and recycling of the epichlorohydrin phase, which had been freed of the water, to the reaction mixture, was commenced. In carrying out this example, a further dehydrochlorination was used.

A bisphenol A-glycidyl ether having an epoxide equivalent of 177, a viscosity of 7,380 cP, measured at 25°C, an 0.08% by weight content of easily saponifiable chlorine and a Hazen colour index of 40 was obtained.

EXAMPLE 5

Example 1 was repeated with the modification that instead of 124 g of sodium hydroxide a mixture of 118 g of sodium hydroxide and 6 g of anhydrous sodium carbonate was employed. In carrying out this example, a further dehydrochlorination was used.

A bisphenol A-glycidyl ether having an epoxide equivalent of 175, a viscosity of 6,980 cP measured at 25°C, an 0.1% by weight content of easily saponifiable chlorine and a Hazen colour index of 30 was obtained.

EXAMPLE 6

Example 1 was repeated with the modifications that
1. in the 1st hour of addition of the sodium hydroxide, ¼ of the total amount of sodium hydroxide was added uniformly, and in the 2nd hour of the addition of sodium hydroxide ¾ of the total amount of sodium hydroxide was added uniformly and
2. the further dehydrochlorination was dispensed with.

A bisphenol A-glycidyl ether having an epoxide equivalent of 175, a viscosity of 7,410 cP measured at 25°C, an 0.04% by weight content of easily saponifiable chlorine and a Hazen colour index of 40 was obtained.

EXAMPLE 7

Example 1 was repeated with the modifications that
1. in the 1st hour of addition of the sodium hydroxide, ¾ of the total amount of sodium hydroxide was added uniformly, and in the 2nd hour of the addition of sodium hydroxide ¼ of the total amount of sodium hydroxide was added uniformly and
2. the further dehydrochlorination was dispensed with.

A bisphenol A-glycidyl ether having an epoxide equivalent of 180, a viscosity of 7,830 cP measured at 25°C, an 0.10% by weight content of easily saponifiable chlorine and a Hazen colour index of 35 was obtained.

EXAMPLE 8

Example 1 was repeated with the modifications that
1. in total only 119 g of sodium hydroxide (NaOH content at least 98% by weight) were added, 2. in the 1st hour of addition of sodium hydroxide ¾ of the total amount was added uniformly and in the 2nd hour of the addition of sodium hydroxide ¼ of the total amount of sodium hydroxide was added uniformly and 3. all process stages which were not carried out in vacuo were carried out under a nitrogen atmosphere. In carrying out this example, further dehydrochlorination was used.

A bisphenol A-glycidyl ether having an epoxide equivalent of 172, a viscosity of 7,530 cP measured at 25°C, and an 0.09% by weight content of easily saponifiable chlorine and a Hazen colour index of 25 was obtained.

EXAMPLE 9

Example 1 was repeated with the modifications that a total of 119 g of sodium hydroxide (NaOH content at least 98% by weight) was added over the course of 3 hours in such a way that ½ the total amount was added uniformly in the 1st hour of addition of sodium hydroxide and the other ½ of the total amount of sodium hydroxide was added uniformly over the course of the further 2 hours of the addition of sodium hydroxide. In carrying out this example, further dehydrochlorination was used.

A bisphenol A-glycidyl ether having an epoxide equivalent of 178, a viscosity of 7,550 cP measured at 25°C, an 0.1% by weight content of easily saponifiable chlorine and a Hazen colour index of 35 was obtained.

EXAMPLE 10

Example 1 was repeated with the modification that instead of 124 g of sodium hydroxide first 118 g of sodium hydroxide (total NaOH content at least 98% by weight) and then 6 g of anhydrous sodium carbonate were added to the reaction mixture uniformly over the course of 2 hours. In carrying out this example, further dehydrochlorination was used. After working up the glycidyl ether, 20 g of deionised water were added dropwise over the course of 30 minutes under a vacuum of approx. 17 mm Hg, at 120°C, under which conditions all the volatile constituents could be trapped in a receiver. Thereafter the contents of the flask were left for a further 15 minutes at 120°C under the same vacuum.

A bisphenol A-glycidyl ether having an epoxide equivalent of 175, a viscosity of 8,750 cP measured at 25°C, an 0.05% by weight content of easily saponifiable chlorine and a Hazen colour index of 35 was obtained.

EXAMPLE 11

330 g of bisphenol A, 1,570 g of epichlorohydrin, 25 g of xylene, 40 g of water, 0.5 g of Sn(NO$_3$)$_2$ and 2 ml of a 70% strength by weight aqueous chlorine chloride solution were warmed to 95°C whilst stirring under a nitrogen atmosphere and left at this temperature for 2 hours. A total of 119 g of sodium hydroxide (NaOH content at least 98% by weight) was then added over the course of 2 hours in such a way that ⅔ of the amount of sodium hydroxide was added uniformly over the course of the 1st hour and the remaining ⅓ of the amount of sodium hydroxide was added uniformly over the course of the 2nd hour. 30 minutes after starting the addition of sodium hydroxide, the azeotropic circulatory dehydration was commenced, with recycling of the epichlorohydrin, which had been freed of the water, to the reaction mixture. After completion of the addition of sodium hydroxide, excess epichlorohydrin was removed under a vacuum of 17 mm Hg whilst raising the temperature to a maximum of 120°C. The residue was dissolved in 500 g of xylene and subjected to a further dehydrochlorination with 660 g of water and 30 g of sodium hydroxide (NaOH content at least 98% by weight) for 1 hour at approx. 95°C under a reflux condenser. The aqueous phase was discarded. The xylene phase was adjusted to a pH value of 6.7 with dilute phosphoric acid, dehydrated by azeotropic circulatory distillation, filtered and freed of the xylene in vacuo, the temperature being raised to a maximum of 120°C.

After filtration, a bisphenol A-glycidyl ether having an epoxide equivalent of 180, a viscosity of 8,100 cP measured at 25°C, an 0.1% by weight content of easily saponifiable chlorine and a Hazen colour index of 30 was obtained.

EXAMPLE 12

468 g of bisphenol A, 24.6 g of a phenol novolak prepared from phenol and formaldehyde by acid condensation and having the average formula

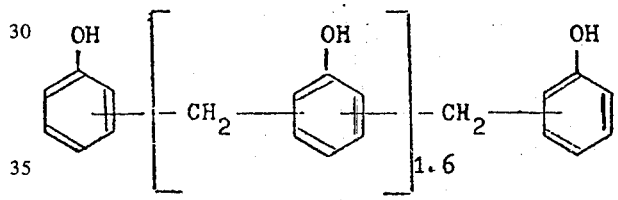

2,010 g of epichlorohydrin, 40 g of xylene, 60 g of water, 2.5 ml of a 70% strength by weight aqueous chlorine chloride solution and 0.6 g of SnCl$_2$.2H$_2$O were heated to 95°C for 2 hours. At the same temperature, 178.5 g of sodium hydroxide (NaOH content at least 98% by weight) were added over the course of 2 hours in such a way that ⅔ of the amount was added uniformly over the course of the 1st hour and ⅓ of the amount was added uniformly over the course of the 2nd hour. 30 minutes after starting the addition, the reaction mixture was azeotropically dehydrated at 95°C under a slight vacuum, and the epichlorohydrin phase freed of the water was recycled to the reaction mixture.

After completion of the addition of sodium hydroxide, excess epichlorohydrin was distilled off under a vacuum of approx. 20 mm Hg whilst raising the temperature to a maximum of 120°C. The residue was dissolved in 750 g of xylene and subjected to a further dehydrochlorination with 990 g of water and 45 g of sodium hydroxide (NaOH content at least 98% by weight) for 1 hour at 70°C. The aqueous phase was discarded and the xylene phase was adjusted to pH 6.8 with 10% strength by weight aqueous NaH$_2$PO$_4$ solution and subjected to circulatory dehydration. After filtration, the xylene was distilled off under a vacuum of 20 mm Hg at temperatures up to a maximum of 120°C. 36 g of water were added uniformly over the course of 30 minutes under the same pressure, at 120°C, whilst trapping all the volatile constituents in a receiver. After again filtering the mixture through a filter candle, a glycidyl ether having an epoxide equivalent of 182, a viscosity of 10,850 cP, measured at 25°C, an 0.10% by weight content of easily saponifiable chlorine and a Hazen colour index of 50 was obtained.

EXAMPLE 13

1,650 g of epichlorohydrin, 50 g of water, 1.65 g of chlorine chloride solution (70% strength by weight in water), 1.0 g of $SnCl_2.2H_2O$ and 330 g of bisphenol A were kept at 95°C for 4 hours. 16.5 g of sodium hydroxide (NaOH content at least 98% by weight) were added uniformly over the course of 20 minutes at this temperature, whilst stirring. Thereafter, 99 g of sodium hydroxide (NaOH content at least 98% by weight) were added uniformly, whilst stirring, and simultaneously subjecting the mixture to circulatory dehydration, and recycling of the epichlorohydrin phase which had been freed of water to the reaction mixture, at 90° to 95°C. After completion of the addition of sodium hydroxide, the excess epichlorohydrin was distilled off whilst reducing the pressure down to approx. 20 mm Hg and raising the temperature to a maximum of 120°C. The residue was dissolved in 470 g of xylene. The sodium chloride formed was dissolved out with 660 g of water. The salt phase was discarded. The xylene phase was postdehalogenated with a solution of 35 g of sodium hydroxide (NaOH content at least 98% by weight) in 330 g of water for 2 hours at 70°C, whilst stirring vigorously. The aqueous phase was then discarded. The xylene phase was adjusted to a pH value of 5.5 with dilute aqueous phosphoric acid. The mixture was dehydrated by circulatory distillation and the anhydrous solution was filtered and concentrated under a reduced pressure of approx. 17 mm Hg whilst raising the temperature to a maximum of 120°C. Under these conditions, approx. 15 g of water were added dropwise over the course of 1 hour to the mixture, and the volatile constituents were trapped in a receiver. The residue was left for a further ½ hour at 120°C under a vacuum of approx. 17 mm Hg and was then filtered through a filter candle.

A bisphenol A-diglycidylether having an epoxide equivalent of 176, a viscosity of 7,720 cP measured at 25°C, an 0.07% by weight content of easily saponifiable chlorine and a Hazen colour index of 40 was obtained.

EXAMPLE 14

Example 13 was repeated with the modification that instead of 330 g of bisphenol A mixture of 85 g of bisphenol A and 218 g of bisphenol F (isomer mixture) was employed.

A bisphenol-diglycidyl ether having an epoxide equivalent of 171, a viscosity of 2,710 cP measured at 25°C, an 0.05% by weight content of easily saponifiable chlorine and a Hazen colour index of 45 was obtained.

EXAMPLE 15

Example 13 was repeated with the modification that instead of 330 g of bisphenol A 228 g of bisphenol F (isomer mixture) were employed.

A bisphenol F-diglycidyl ether having an epoxide equivalent of 167, a viscosity of 1,900 cP measured at 25°C, an 0.05% by weight content of easily saponifiable chlorine and a Hazen colour index of 45 was obtained.

EXAMPLE 16

Example 13 was repeated with the modification that instead of 330 g of bisphenol A, 248 g of bisphenol A and 75 g of bisphenol F (isomer mixture) were employed.

A bisphenol-diglycidyl ether having an epoxide equivalent of 173, a viscosity of 5,650 cP measured at 25°C, an 0.08% by weight content of easily saponifiable chlorine and a Hazen colour index of 35 was obtained.

EXAMPLE 17

Example 13 was repeated with the modification that instead of 1,650 g of epichlorohydrin 1,070 g of epichlorohydrin were employed.

A bisphenol A-glycidyl ether having an epoxide equivalent of 190, a viscosity of 11,900 cP measured at 25°C, an 0.05% by weight content of easily saponifiable chlorine and a Hazen colour index of 30 was obtained.

EXAMPLE 18

985 g of epichlorohydrin, 36 g of i-butanol, 26 g of xylene, 24 g of water, 0.7 ml of an aqueous 75% strength by weight choline chloride solution and 0.21 g of $SnCl_2.2H_2O$ were freed of atmospheric oxygen in a three-neck flask, by passing in $N_2$. 210 g of p-tert. butylphenol were added whilst continuing to introduce $N_2$. The mixture was warmed to 95°C under reflux, whilst stirring, and left at this temperature for 60 minutes. 25.5 g of sodium hydroxide (NaOH content at least 98% by weight) were then added in uniform portions over the course of approx. 60 minutes at approx 95°C, under reflux, whilst continuing to introduce $N_2$. Thereafter, a further 30 g of sodium hydroxide (NaOH content at least 98% by weight) were added uniformly to the mixture under normal pressure or a slight vacuum at approx. 95°C, with simultaneous circulatory dehydration and recycling of the epichlorohydrin phase, which had been freed of the water, to the mixture. After completion of the addition of sodium hydroxide, excess epichlorohydrin and solvent were distilled off under a vacuum of approx. 20 mm Hg, with the temperature rising to a maximum of 120°C. The residue freed of the epichlorohydrin was dissolved in 350 g of xylene and 320 g of water and 15 g of sodium hydroxide (NaOH content at least 98% by weight) were added and the whole warmed to the reflux temperature for 60 minutes. The aqueous phase was removed and the xylene phase was adjusted to a pH value of approx. 6.5 with dilute phosphoric acid. Xylene and water were removed by distillation, whilst raising the temperature to 150°C under a vacuum of approx. 17 mm Hg. After this temperature had been maintained for a further hour, the mixture was filtered following addition of 3 g of a filtration aid resembling kieselguhr. A p-tert. butylphenyl-glycidyl ether having an epoxide equivalent of 216, a viscosity of 17 cP, measured at 25°C, an 0.05% by weight content of easily saponifiable chlorine and a Hazen colour index of 25 was obtained.

The process according to the invention explained in the preceding Examples 1–11 and 13–17 yields the diglycidyl ethers of bisphenol A or bisphenol F to the extent of approx. 90% by weight. The remaining proportion consists essentially of polyglycidyl ethers of the corresponding bisphenols of the general formula

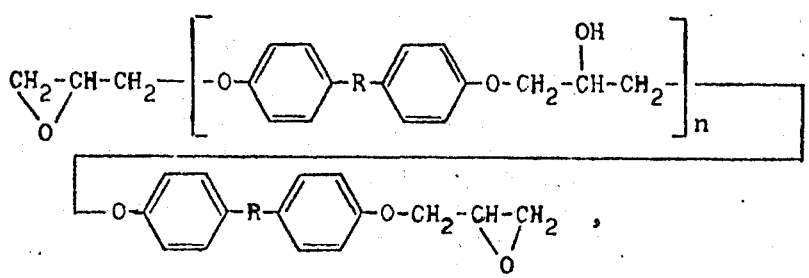

wherein the degree of condensation $n$ can assume the values 1 to 10 and —R— can denote the —C(CH$_3$) or —CH$_2$— groups.

In Example 12, a proportion of 5% by weight of the polyglycidyl ether of the phenol novola (sic) characterised in more detail in Example 12, is also produced.

In Example 18, the monoglycidyl ether of p-tert. butylphenol is produced to the extent of approx. 90% by weight, in addition to a proportion of unidentified by-products.

In its individual stages, the process according to the invention takes place through at least 10%, preferably 50 - 90%, relative to the phenolic hydroxyl group, of chlorohydrin ethers being produced in stage a), which are converted to a slight extent into glycidyl ethers by transepoxidation by the excess epichlorohydrin. In stage b), the catalytic action of the quaternary ammonium compound and of the added alkali metal hydroxide effects the final formation of the chlorohydrin ether in addition to an incipient dehydrochlorination by the alkali metal hydroxide, to give glycidyl ethers. In stage (c), extensive dehydrochlorination by the alkali metal hydroxide to give the glycidyl ether occurs, with the equilibrium being displaced towards the glycidyl ether through the removal of the water of reaction by circulatory dehydration:

($R$ = aromatic radical).

This would substantially reduce the yield and make the isolation of the glycidyl ether more difficult. Furthermore, since only the monomeric chlorohydrin ether is present from the start during the addition of the alkali metal hydroxide, the formation of a largely monomeric glycidyl ether is also ensured.

The circulatory dehydration in stage c) favours the formation of glycidyl ethers which have a particularly low content of easily saponifiable chlorine.

The following Examples 19 to 29 demonstrate the method in which in stage (c) the reaction water distilled off (optionally the added water) and the liquid phase containing the non-reacted epichlorohydrin, which was freed from water, are not recycled to the reaction mixture.

EXAMPLE 19

330 g of bisphenol A, 1,610 g of epichlorohydrin, 32 g of xylene, 48 g of water, 0.33 g of SnCl$_2$.2H$_2$O and 1.5 ml of choline chloride, as a 70% strength solution in water, were warmed for 2 hours to 95°C in a three-neck flask. 89 g of sodium hydroxide (approx. 98% strength by weight) were then added uniformly distributed over one hour, at the same temperature, the reaction mixture being kept under a reflux condenser. 30 g of so-

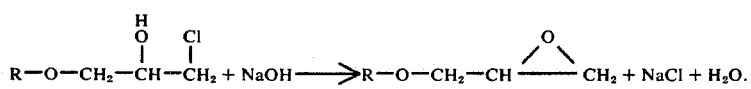

Stage (d) also serves to effect a post-dehydrochlorination if the content of easily saponifiable chlorine is more than 0.1% by weight.

Carrying out the process in this way prevents the formation of higher-molecular sparingly soluble phenoxyethers, which can easily occur if the reaction velocity of the formation of the chlorohydrin ethers is too low and glycidyl ethers and phenols are simultaneously present in the alkaline medium:

dium hydroxide (approx. 98% strength by weight) were added uniformly in small portions over the course of a further 2 hours whilst simultaneously removing water and epichlorohydrin as an azeotrope under a pressure which was initially 740 mm Hg and was 560 mm Hg at the end of the addition, in such a way that in the first hour of the distillation approx. 170 ml of epichlorohydrin and 80 ml of water are separated off and in the second hour approx. 150 ml of epichlorohydrin and 30

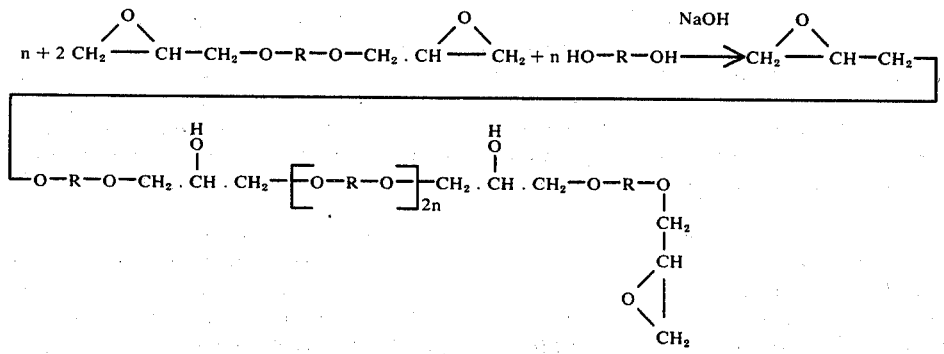

ml of water are separated off. After completion of the addition of sodium hydroxide, excess epichlorohydrin and solvent were removed under a water pump vacuum of approx. 15 mm Hg. The residue was kept under this vacuum at 120°C for approx. 1 hour. It was then dissolved in 50 g of xylene. The sodium chloride formed was washed out with 660 g of water. If the content of saponifiable chlorine in the glycidyl ether obtained is more than 0.1% by weight, a further dehydrochlorination was carried out with 115 g of a 10% strength by weight aqueous sodium hydroxide solution for 1 hour at 95°C. The aqueous phase was removed and the xylene solution was neutralised with dilute phosphoric acid, freed of the water by azeotropic circulatory distillation, filtered and concentrated under a vacuum of approx. 15 mm Hg whilst raising the temperature to 120°C. The bisphenol A-glycidyl ether was left under this vacuum at 120°C for 60 minutes. A bisphenol A-glycidyl ether having an epoxide equivalent of 176, a viscosity of 7,760 cP measured at 25°C, an 0.03% by weight content of easily saponifiable chlorine and a Hazen colour index of 30 was obtained.

EXAMPLE 20

Example 19 was repeated with the modifications that
1. during the first hour of addition of sodium hydroxide, 80 g of sodium hydroxide (approx. 98% strength by weight) were added uniformly under reflux and during the further two hours of the addition of sodium hydroxide, 39 g of sodium hydroxide (approx. 98% strength by weight) were added uniformly whilst simultaneously removing a mixture of water and epichlorohydrin by azeotropic distillation and
2. it was possible to dispense with the further dehydrochlorination. A bisphenol A-glycidyl ether having an epoxide equivalent of 176, a viscosity of 7,100 cP measured at 25°C, an 0.08% by weight content of easily saponifiable chlorine and a Hazen colour index of 35 was obtained.

EXAMPLE 21

Example 19 was repeated with the modifications that
1. the reaction mixture did not contain any xylene and
2. before starting the addition of sodium hydroxide, the mixture was kept for 3 hours at 95°C. In carrying out this example, further dehydrochlorination was used. A bisphenol A-glycidyl ether having an epoxide equivalent of 175, a viscosity of 8,200 cP measured at 25°C, a content of easily saponifiable chlorine of less than 0.1% by weight and a Hazen colour index of 30 was obtained.

EXAMPLE 22

330 g of bisphenol A, 1,570 g of epichlorohydrin, 25 g of xylene, 40 g of water, 0.5 g of Sn(NO$_3$)$_2$ and 2 ml of a 70% strength by weight aqueous choline chloride solution were warmed to 95°C under a nitrogen atmosphere whilst stirring and left at this temperature for 2 hours. 85 g of sodium hydroxide (approx. 98% strength by weight) were then added, uniformly distributed over 1 hour, at the same temperature, whilst keeping the reaction mixture under a reflux condenser. 39 g of sodium hydroxide (approx. 98% strength by weight) were added uniformly in small portions over the course of a further two hours whilst at the same time removing water and epichlorohydrin as an azeotrope under a pressure which was initially 740 mm Hg and was 560 mm Hg at the end of the addition, in such a way that during the first hour of distillation approx. 180 ml of epichlorohydrin and 78 ml of water, and in the second hour approx. 160 ml of epichlorohydrin and 35 ml of water are separated off. After completion of the addition of sodium hydroxide, excess epichlorohydrin was removed under a vacuum of 17 mm Hg whilst raising the temperature to a maximum of 120°C. The residue was dissolved in 500 g of xylene and subjected to a further dehydrochlorination with 660 g of water and 30 g of sodium hydroxide (NaOH content at least 98% by weight) for one hour at approx. 95°C under a reflux condenser. The aqueous phase was discarded and the xylene phase was adjusted to a pH value of 6.7 with dilute phosphoric acid, dehydrated by azeotropic circulatory distillation, filtered and freed of the xylene in vacuo up to a maximum temperature of 120°C.

After filtration, a bisphenol A-glycidyl ether having an epoxide equivalent of 181, a viscosity of 8,500 cP measured at 25°C, an 0.1% by weight content of easily saponifiable chlorine and a Hazen colour index of 30 was obtained.

EXAMPLE 23

468 g of bisphenol A, 24.6 g of a phenol novolak prepared from phenol and formaldehyde by acid condensation and having the average formula

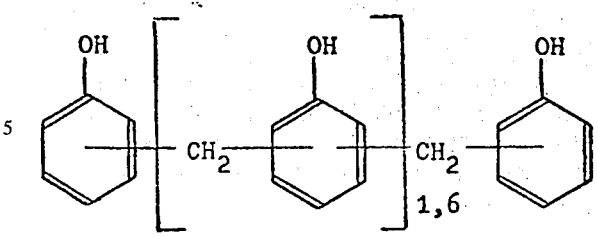

2,010 g of epichlorohydrin, 40 g of xylene, 60 g of water, 2.5 ml of a 70% strength by weight aqueous choline chloride solution and 0.6 g of SnCl$_2$.2H$_2$O were heated to 95°C for 2 hours. 134.5 g of sodium hydroxide (approx. 98% strength by weight) were added uniformly over the course of 1 hour at the same temperature whilst keeping the reaction mixture under a reflux condenser. 44.5 g of sodium hydroxide (approx. 98% strength by weight) were added uniformly in small portions over the course of a further two hours whilst simultaneously removing water and epichlorohydrin as an azeotrope, under a pressure which was initially 740 mm Hg and was 560 mm Hg at the end of the addition, in such a way that in the first hour of distillation approx. 260 ml of epichlorohydrin and 120 ml of water are separated off and in the second hour approx. 230 ml of epichlorohydrin and 45 ml of water are separated off. After completion of the addition of sodium hydroxide, excess epichlorohydrin was distilled off under a vacuum of approx. 20 mm Hg whilst raising the temperature to a maximum of 120°C. The residue was dissolved in 750 g of xylene and subjected to a further dehydrochlorination with 990 g of water and 45 g of sodium hydroxide (NaOH content at least 98% by weight) for 1 hour at 70°C. The aqueous phase was discarded and the xylene phase was adjusted to pH 6.8 with 10% strength by weight aqueous NaH$_2$PO$_4$ solution and subjected to circulatory dehydration. After filtration, the xylene was distilled off under a vacuum of 20 mm Hg at a temperature rising to a maximum of 120°C. At 120°C, 36 g of water were added dropwise uniformly over 30 minutes under the same pressure, all the volatile constituents being trapped in a receiver. After renewed filtration through a filter candle, a glycidyl ether having an epoxide equivalent of 183, a viscosity of 10,500 cP measured at 25°C, an 0.10% by weight content of easily saponifiable chlorine and a Hazen colour index of 45 was obtained.

EXAMPLE 24

1,650 g of epichlorohydrin, 50 g of water, 1.65 g of choline chloride solution (70% strength by weight in water), 1.0 g of $SnCl_2.2H_2O$ and 330 g of bisphenol A were kept at 95°C for 4 hours. 89 g of sodium hydroxide (approx. 98% strength by weight) were added uniformly over the course of one hour at this temperature, whilst keeping the reaction mixture under a reflux condenser. 32 g of sodium hydroxide (approx. 98% strength by weight) were added uniformly in small portions over the course of a further 2 hours whilst at the same time water and epichlorohydrin were removed as an azeotrope under a pressure which was initially 740 mm Hg and was 560 mm Hg at the end of the addition, in such a way that during the first hour of distillation approx. 179 ml of epichlorohydrin and 82 ml of water are separated off and in the second hour approx. 155 ml of epichlorohydrin and 28 ml of water are separated off. After completion of the addition of sodium hydroxide, the excess epichlorohydrin was distilled off whilst reducing the pressure down to approx. 20 mm Hg and raising the temperature to 120°C. The residue was dissolved in 470 g of xylene. The sodium chloride formed was dissolved out with 660 g of water. The salt phase was discarded. The xylene phase was postdehalogenated with a solution of 35 g of sodium hydroxide (approx. 98% strength by weight) in 330 g of water for 2 hours at 70°C whilst stirring thoroughly. Thereafter, the aqueous phase was discarded. The xylene phase was adjusted to a pH value of 5.5 with dilute aqueous phosphoric acid. It was dehydrated by circulatory distillation and the anhydrous solution was filtered and concentrated under reduced pressure at approx. 17 mm Hg whilst raising the temperature to a maximum of 120°C. Under these conditions, approx. 15 g of water were added dropwise to the mixture over the course of 1 hour whilst collecting the volatile constituents in a receiver. The residue was left at 120°C under a vacuum of approx. 17 mm Hg for a further ½ hour and was then filtered through a filter candle. A bisphenol A-diglycidyl ether having an epoxide equivalent of 177, a viscosity of 8,200 cP measured at 25°C, an 0.08% by weight content of easily saponifiable chlorine and a Hazen colour index of 35 was obtained.

EXAMPLE 25

Example 24 was repeated with the modification that instead of 330 g of bisphenol A a mixture of 85 g of bisphenol A and 218 g of bisphenol F (isomer mixture) was employed.

A bisphenol-diglycidyl ether having an epoxide equivalent of 172, a viscosity of 2,850 cP measured at 25°C, an 0.05% by weight content of easily saponifiable chlorine and a Hazen colour index of 45 was obtained.

EXAMPLE 26

Example 24 was repeated with the modification that instead of 330 g of bisphenol A, 288 g of bisphenol F (isomer mixture) were employed.

A bisphenol F-diglycidyl ether having an epoxide equivalent of 166, a viscosity of 1,950 cP measured at 25°C, an 0.05% by weight content of easily saponifiable chlorine and a Hazen colour index of 45 was obtained.

EXAMPLE 27

Example 24 was repeated with the modification that instead of 330 g of bisphenol A, 248 g of bisphenol A and 75 g of bisphenol F (isomer mixture) were employed.

A bisphenol-diglycidyl ether having an epoxide equivalent of 174, a viscosity of 5,900 cP measured at 25°C, an 0.07% by weight content of easily saponifiable chlorine and a Hazen colour index of 35 was obtained.

EXAMPLE 28

Example 24 was repeated with the modification that instead of 1,650 g of epichlorohydrin, 1,070 g of epichlorohydrin were employed.

A bisphenol A-glycidyl ether having an epoxide equivalent of 189, a viscosity of 12,300 cP measured at 25°C, an 0.05% by weight content of easily saponifiable chlorine and a Hazen colour index of 30 was obtained.

EXAMPLE 29

985 g of epichlorohydrin, 36 g of i-butanol, 26 g of xylene, 24 g of water, 0.7 ml of an aqueous 75% strength by weight choline chloride solution and 0.21 g of $SnCl_2.2H_2O$ were freed of atmospheric oxygen by passing $N_2$ through them in a three-neck flask. 210 g of p-tert.-butylphenol were added whilst continuing the supply of $N_2$. The mixture was warmed to 95°C under reflux, whilst stirring, and kept at this temperature for 60 minutes. 42 g of sodium hydroxide (approx. 98% strength by weight) were then added in uniform portions over the course of approx. 60 minutes whilst continuing the supply of $N_2$, the reaction mixture being kept under a reflux condenser. 13.5 g of sodium hydroxide (approx. 98% strength by weight) were added uniformly in small portions over the course of a further two hours whilst simultaneously removing water and epichlorohydrin as an azeotrope under a pressure which was initially 740 mm Hg and was 560 mm Hg at the end of the addition, in such a way that during the first hour of the distillation approx. 80 ml of epichlorohydrin and 38 ml of water are separated off and in the second hour approx. 70 ml of epichlorohydrin and 14 ml of water are separated off. After completion of the addition of sodium hydroxide, excess epichlorohydrin and solvent were distilled off under a vacuum of approx. 20 mm Hg whilst raising the temperature to a maximum of 120°C. The residue freed of the epichlorohydrin was dissolved in 350 g of xylene, 320 g of water and 15 g of sodium hydroxide (NaOH content at least 98% by weight) were added and the mixture was warmed to the reflux temperature for 60 minutes. The aqueous phase was removed and the xylene phase was adjusted to a pH value of approx. 6.5 with dilute phosphoric acid. The xylene and water were removed by distillation, whilst raising the temperature to 150°C under a vacuum of approx. 17 mm Hg. After this temperature had been maintained for a further hour, 3 g of a filtration aid resembling kieselguhr were added and the mixture was then filtered.

A p-tert.-butylphenyl-glycidyl ether having an epoxide equivalent of 218, a viscosity of 18 cP measured at 25°C, an 0.05% by weight content of easily saponifiable chlorine and a Hazen colour index of 25 was obtained.

What is claimed is:

1. In a process for manufacturing glycidyl ethers from monohydric or polyhydric phenols and excess epichlorohydrin, relative to the amount of phenolic hydroxyl groups, in the presence of a catalyst which is specific for the formation of chlorohydrin ethers from the phenol and epichlorohydrin and from 0.2 to 8 percent by weight of water, based upon the weight of the reaction medium, and then the chlorohydrin is reacted by heating with 0.9 to 1.15 equivalent of solid alkali metal hydroxide per phenolic hydroxyl group to give glycidyl ethers in the presence of 0.001 to 5 percent by weight, based on the amount of phenol employed, of a divalent tin compound, the improvement which comprises
   a. in the first stage, conducting the reaction between phenol and the excess epichlorohydrin in the presence of the catalyst specific to the formation of the chlorohydrin in an alkali-free medium at from 50° to 100°C for from 1 to 4 hours, until 50 to 90 percent, based on the phenolic hydroxyl groups, of the chlorohydrin is formed, and thereafter
   b. in a second stage, adding to the reaction mixture from stage (a) from 10 to 90 percent by weight of the solid alkali metal hydroxide over the course of 18 to 90 percent of the total time of addition of the solid alkali metal hydroxide, which time is 30 to 300 minutes, while removing the heat of reaction by cooling the mixture or distillation under reflux under reduced pressure in the presence of water of reaction or added water, and thereafter
   c. in a third stage, adding the remainder of the solid alkali metal hydroxide, with removal of the heat of reaction and water of reaction or added water from the mixture by azeotropic distillation, and thereafter
   d. distilling the excess epichlorohydrin from the glycidyl ether product.

2. Method according to claim 1, characterized in that in stage (c) the azeotropic distillation is carried out by recycling the phase containing epichlorohydrin, which had been freed from water, to the reaction mixture.

3. Method according to claim 1, characterized in that as divalent tin-compounds forming stannites ($Me'_2[Sn(OH)_4]$ or $Me'[Sn(OH)_3]$) with alkalis, such as $SnCl_2$, $Me'[SnCl_3]$, $SnCl_2 \cdot 2H_2O$, $SnF_2$, $SnBr_2$, $SnJ_2$, $Sn(OH)_2$, $SnSO_4$, $Sn(NO_3)_2$, $Sn(SCN)_2$, $SnC_2O_4$ (oxalate) and salts of divalent tin with organic acids, of the formula $Sn(OOCR)_2$, wherein —R can be an alkyl or iso-alkyl radical with 1 to 12 carbon atoms, or the stannites themselves are employed.

4. Method according to claim 1, characterized in that in the reaction 3 to 15, preferably 4 to 12 mols epichlorohydrin are used per phenolic hydroxyl group.

5. Method according to claim 1, characterized in that as catalyst specific for the formation of chlorohydrin ethers choline or choline salts or/and further quaternary ammonium salts are employed.

6. Method according to claim 1, characterized in that the liquid glycidyl ether is freed from the organic solvents by steam distillation at 100° to 160°C.

7. The method according to claim 1 characterized in that volatile components are removed from the liquid glycidyl ether by heating the mixture to from 100°C to 180°C and by adding from 1 to 10 percent by weight, relative to the glycidyl ether, of aqueous hydrogen peroxide solution containing from 1 to 20 percent by weight of hydrogen peroxide, while stirring the mixture.

8. The method according to claim 1 characterized in that in stage (c) the azeotropic distillation is carried out without recycling water of reaction, added water, unreacted epichlorohydrin or the liquid phase containing epichlorohydrin which has been freed from the water.

* * * * *

UNITED STATES PATENT OFFICE
CERTIFICATE OF CORRECTION

Patent No. 3,980,679          Dated September 14, 1976

Inventor(s) Wilhelm Becker

It is certified that error appears in the above-identified patent and that said Letters Patent are hereby corrected as shown below:

| In the Patent: | Should read: |
|---|---|
| Col. 2, Line 3: "comounds" | --- compounds --- |
| Col. 2, Line 6: "muct" | --- much --- |
| Col. 2, Line 13: "accordingn" | --- according --- |
| Col. 2, Line 17: "25" | --- 26 --- |
| Col. 3, Lines 15-16: "chlorophydrin" | --- chlorohydrin --- |
| Col. 6, Line 40: "azetropic" | --- azeotropic --- |
| Col. 9, Line 54: "chlorine" | --- choline --- |

UNITED STATES PATENT OFFICE
CERTIFICATE OF CORRECTION

Patent No. 3,980,679　　　　　　　　Dated September 14, 1976

Inventor(s) Wilhelm Becker

It is certified that error appears in the above-identified patent and that said Letters Patent are hereby corrected as shown below:

| In the Patent: | Should read: |
|---|---|
| Col. 10, Line 45: "chlorine" | --- choline --- |
| Col. 11, Line 13: "chlorine" | --- choline --- |
| Col. 11, Line 55: "A mixture" | --- A a mixture --- |
| Col. 15, Line 6: "50g" | --- 500g --- |

Signed and Sealed this

Seventh Day of December 1976

[SEAL]

Attest:

RUTH C. MASON
Attesting Officer

C. MARSHALL DANN
Commissioner of Patents and Trademarks